United States Patent
Lei et al.

(10) Patent No.: US 11,875,901 B2
(45) Date of Patent: Jan. 16, 2024

(54) REGISTRATION APPARATUS, REGISTRATION METHOD, AND RECORDING MEDIUM

(71) Applicant: Hitachi, Ltd., Tokyo (JP)

(72) Inventors: Miaomei Lei, Tokyo (JP); Takahiro Nakamura, Tokyo (JP); Daisuke Suzuki, Tokyo (JP); Takashi Takemoto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 348 days.

(21) Appl. No.: 17/198,661

(22) Filed: Mar. 11, 2021

(65) Prior Publication Data

US 2022/0093265 A1 Mar. 24, 2022

(30) Foreign Application Priority Data

Sep. 23, 2020 (JP) .................. 2020-158316

(51) Int. Cl.
| | |
|---|---|
| *G16H 50/50* | (2018.01) |
| *G06N 20/00* | (2019.01) |
| *G16H 30/20* | (2018.01) |
| *G06F 18/22* | (2023.01) |
| *G06F 18/213* | (2023.01) |

(52) U.S. Cl.
CPC ............ *G16H 50/50* (2018.01); *G06N 20/00* (2019.01); *G16H 30/20* (2018.01); *G06F 18/213* (2023.01); *G06F 18/22* (2023.01)

(58) Field of Classification Search
CPC .............................................. G06Q 50/20–26
See application file for complete search history.

(56) References Cited

U.S. PATENT DOCUMENTS

| | | | |
|---|---|---|---|
| 2007/0178473 A1* | 8/2007 | Chen ................... | G16B 5/00 702/20 |
| 2008/0249966 A1* | 10/2008 | Luege Mateos .... | G06F 16/3347 707/999.005 |

(Continued)

FOREIGN PATENT DOCUMENTS

| | | | | |
|---|---|---|---|---|
| EP | 3306617 A1 * | 4/2018 | ........... | A61B 5/0022 |
| EP | 3599617 A1 * | 1/2020 | ......... | G06F 16/2272 |

(Continued)

*Primary Examiner* — Jason S Tiedeman
*Assistant Examiner* — Jessica Marie Webb
(74) *Attorney, Agent, or Firm* — Volpe Koenig

(57) ABSTRACT

A registration apparatus is configured to access a network formed of a set of first nodes and first edges, the first nodes each representing a first feature vector including a plurality of elements, the first edges each coupling two first nodes representing two first feature vectors to each other based on two first feature vectors, a processor in the registration apparatus is configured to execute: obtaining processing of obtaining a second feature vector; and registration processing of registering a second node representing the second feature vector to the network based on a similarity relationship among third feature vectors in a set of third feature vectors included in the set of first feature vectors, and coupling the second node and a third node representing the third feature vector to each other with a second edge, the number of third feature vectors being smaller than the number of first feature vectors.

5 Claims, 15 Drawing Sheets

(56) References Cited

U.S. PATENT DOCUMENTS

| | | | | |
|---|---|---|---|---|
| 2009/0083231 A1* | 3/2009 | Eberholst | ............... | G16H 10/60 |
| | | | | 707/999.102 |
| 2013/0268290 A1* | 10/2013 | Jackson | ................ | G16B 50/10 |
| | | | | 705/2 |
| 2014/0359422 A1* | 12/2014 | Bassett, Jr. | ............ | G16B 20/00 |
| | | | | 707/754 |
| 2016/0148109 A1* | 5/2016 | Watanabe | ............... | G06N 5/047 |
| | | | | 706/48 |
| 2016/0283677 A1* | 9/2016 | Carmeli | ................... | G16B 5/00 |
| 2018/0046762 A1* | 2/2018 | Osetinsky | .............. | G16H 10/60 |
| 2018/0095969 A1* | 4/2018 | Jung | ....................... | G16B 30/00 |
| 2019/0311811 A1* | 10/2019 | Joseph | .................. | G16B 45/00 |
| 2019/0354883 A1* | 11/2019 | Aravamudan | .......... | G06F 40/30 |
| 2020/0075135 A1* | 3/2020 | Otaki | ..................... | G06F 16/285 |
| 2021/0383068 A1* | 12/2021 | Mattivi | .................... | G06N 3/08 |

FOREIGN PATENT DOCUMENTS

| | | | | |
|---|---|---|---|---|
| EP | 3859745 A1 * | 8/2021 | ............. | G16H 50/50 |
| JP | 2019-20946 A | 2/2019 | | |
| WO | WO-2020170052 A1 * | 8/2020 | ............... | G06N 3/04 |

* cited by examiner

REGISTRATION APPARATUS, REGISTRATION METHOD, AND RECORDING MEDIUM

CLAIM OF PRIORITY

The present application claims priority from Japanese patent application JP 2020-158316 filed on Sep. 23, 2020, the content of which is hereby incorporated by reference into this application.

BACKGROUND

This invention relates to a data registration apparatus, a data registration method, and a recording medium.

In JP 2019-20946 A, there is disclosed a leaning data precision visualization system, which is configured to use a dynamic model to visualize correlation among pieces of leaning data being data subjected to natural language analysis. The learning data precision visualization system includes a display unit, a node optimal arrangement calculation processing module, and a display control module. The display unit is configured to execute predetermined display. The node optimal arrangement calculation processing module is configured to use the dynamic model to calculate an optimal arrangement of nodes relating to the learning data being the data subjected to the natural language analysis. The display control module is configured to provide control of visualizing the leaning data based on results of calculation by the node optimal arrangement calculation processing module and displaying the visualized learning data on the display unit.

However, with the leaning data precision visualization system disclosed in JP 2019-20946 A, it is required to execute calculation from the beginning to cluster cohort data having such a characteristic that the data is updated at any time, and a period of time required for calculation thus becomes longer.

SUMMARY

This invention has an object to reduce a calculation period at a time when a network is updated.

An aspect of the invention disclosed in this application is a registration apparatus, comprising: a processor configured to execute a program; and a storage device configured to store the program, wherein the registration apparatus is configured to access a network formed of a set of first nodes and first edges, the first nodes each representing a first feature vector including a plurality of elements, the first edges each coupling two first nodes representing two first feature vectors to each other based on two first feature vectors, wherein the processor is configured to execute: obtaining processing of obtaining a second feature vector; and registration processing of registering a second node representing the second feature vector obtained in the obtaining processing to the network based on a similarity relationship among third feature vectors in a set of third feature vectors included in the set of first feature vectors, and coupling the second node and a third node representing the third feature vector to each other with a second edge, the number of third feature vectors being smaller than the number of first feature vectors.

According to at least one representative embodiment of this invention, it is possible to reduce the calculation period at the time when the network is updated. The details of one or more implementations of the subject matter described in the specification are set forth in the accompanying drawings and the description below. Other features, aspects, and advantages of the subject matter will become apparent from the description, the drawings, and the claims.

DETAILED DESCRIPTION OF THE EMBODIMENTS

<Example of Network Update>

Figure 1:
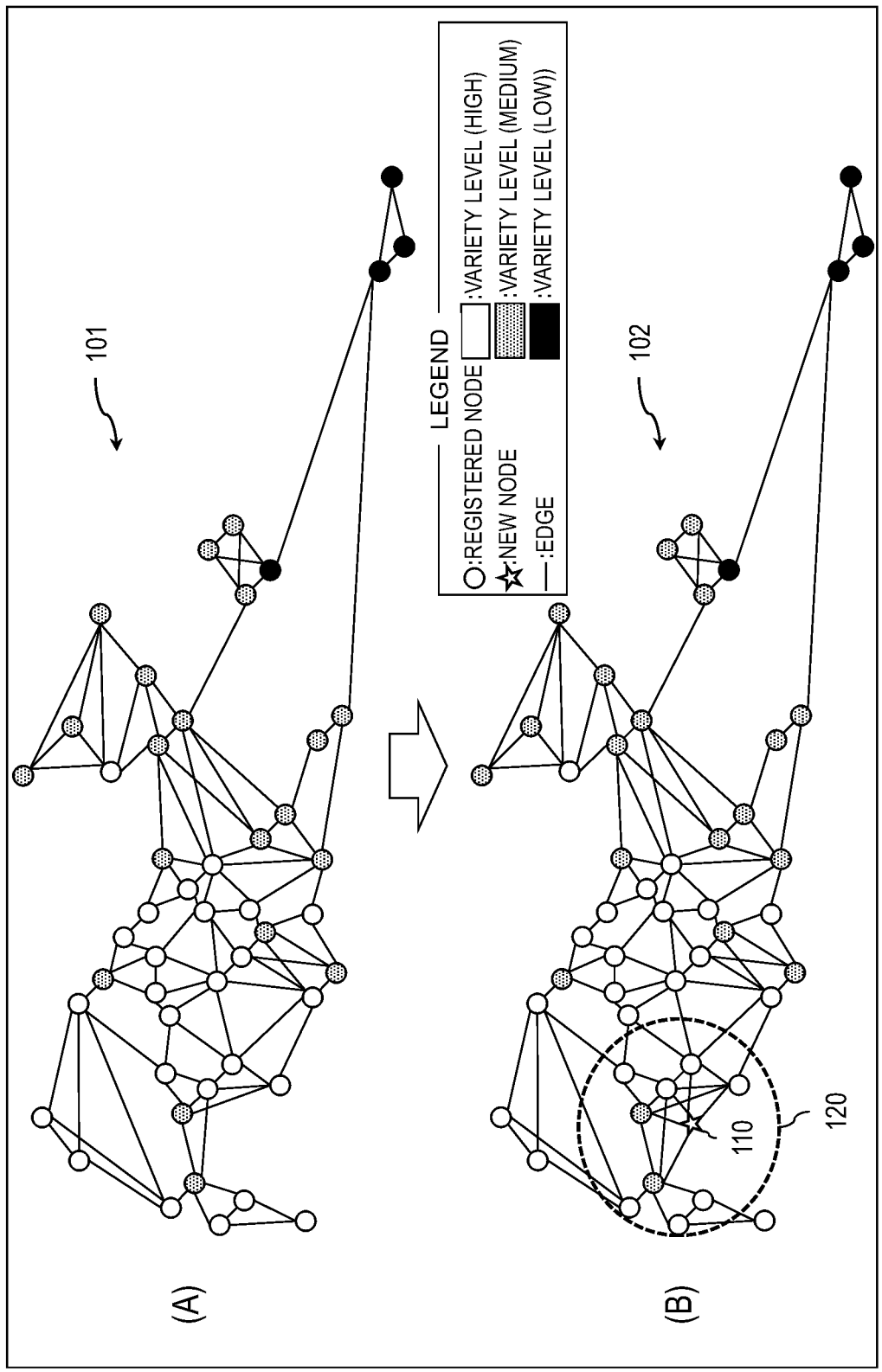
FIG. 1 is an explanatory diagram for illustrating an example of network update based on a dynamic model by a registration apparatus.

FIG. 1 is an explanatory diagram for illustrating an example of network update based on a dynamic model by a registration apparatus. Each of networks 101 and 102 based on the dynamic model is formed of a plurality of nodes and edges, and the edges couple the nodes to each other. The node represents a feature vector having, as elements, feature quantities obtained from attributes of a person, such as types and the number of intestinal bacteria forming an intestinal bacterial flora of the person, meal data on the person (for example, when, what, and how much the person eats and drinks), basic data (for example, the body height, the body weight, and the body fat percentage), and life style data (for example, the amount of drinking alcohol per week and the amount of smoking per week).

The edge represents similarity between nodes at both ends thereof. For example, as the length of the edge becomes shorter, attributes of persons identified by the nodes at both ends become more similar. It should be noted that, a variety level identified by the attributes (elements of the vector) of the person of a node may be associated with the node. The variety level is an index value indicating the number of types of intestinal bacteria. As the number of types of intestinal bacteria increases, the variety level increases.

Part (A) of FIG. 1 shows a network 101 formed of existing nodes. Part (B) of FIG. 1 shows a network 102 after update of adding a new node 110 to the network 101. When the registration apparatus adds the new node 110 to the network 101, the registration apparatus does not generate the network 102, and registers the new node 110 to the network 101, to thereby update the network 101 to the network 102. A position of the registration of the new node 110 depends on correlation between the attributes of the new node 110 and the attributes of the nodes forming the network 101. As a result, compared with a case in which the network 102 is newly generated, a computational load can be reduced, and a calculation period can thus be reduced.

Moreover, a circle 120 is a certain range around the new node 110 as a center. The registration apparatus can execute various predictions for the person corresponding to the new node 110 based on the attributes of existing nodes within the range of the circle 120.

<Hardware Configuration Example>

Figure 2:
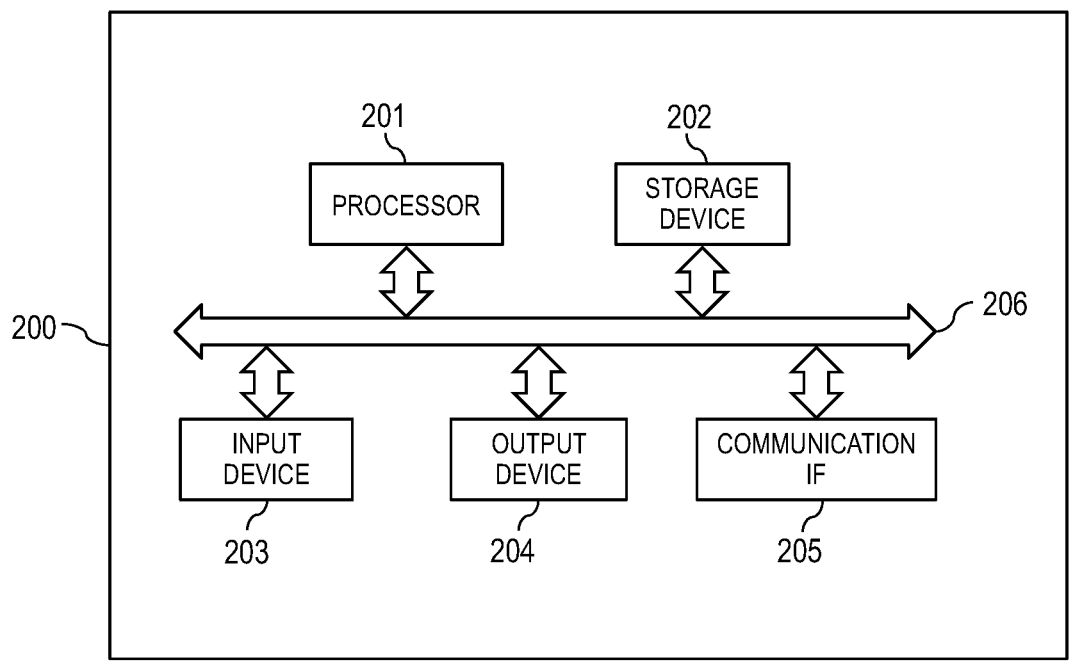
FIG. 2 is a block diagram illustrating a hardware configuration example of a registration apparatus.

FIG. 2 is a block diagram illustrating a hardware configuration example of a registration apparatus. The registration apparatus 200 includes a processor 201, a storage device 202, an input device 203, an output device 204, and a communication interface (communication IF) 205. The processor 201, the storage device 202, the input device 203, the output device 204, and the communication IF 205 are connected to one another by a bus 206. The processor 201 controls the registration apparatus 207. The processor 201 executes various programs. The storage device 202 serves as a work area of the processor 201. The storage device 202 is a non-transitory or temporary recording medium which stores the various programs and data. The storage device 202 can be, for example, a read-only memory (ROM), a random access memory (RAM), a hard disk drive (HDD), or a flash memory. The input device 203 inputs data. The input device 203 can be, for example, a keyboard, a mouse, a touch panel, a ten-key pad, a scanner or a microphone. The output device 204 outputs data. The output device 204 can be, for example, a display, a printer or a speaker. The communication IF 205 couples to a network to transmit and receive data.

It should be noted that the registration apparatus 200 can be implemented as a standalone type or a client/server type. In the case of the client/server type, the registration apparatus 200 serves as a server, and receives various types of input from clients, and outputs data to the clients.

<Various Data Configurations>

With reference to FIG. 3 to FIG. 6, description is now given of various data configurations to be used by the registration apparatus 200. The data configurations of FIG. 3 to FIG. 6 are specifically stored, for example, in the storage device 202 of the registration apparatus 200 or a storage device 202 of a computer that the registration apparatus 200 can access.

Figure 3:
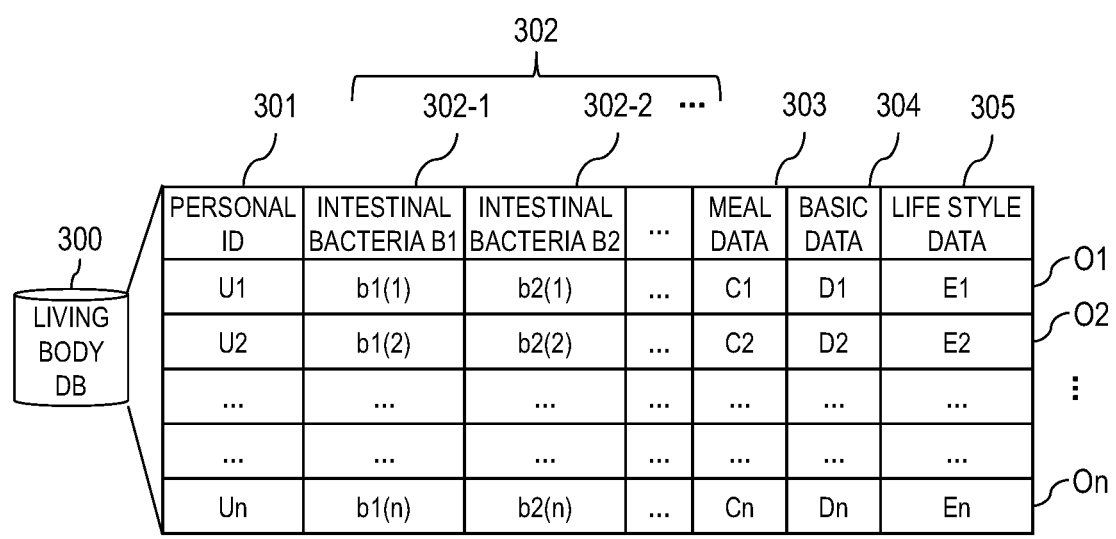
FIG. 3 is an explanatory diagram for illustrating an example of a living body database (DB).

FIG. 3 is an explanatory diagram for illustrating an example of a living body database (DB). A living body DB 300 is stored in the storage device 202. The living body DB 300 includes, as fields, for example, a personal ID 301, an intestinal bacterial flora 302, meal data 303, basic data 304, and life style data 305. A combination of values in the respective fields in one row forms an entry representing each of pieces of living body data O1 to On respective persons (when the living body data are not distinguished from one another, the living body data is simply denoted by "O"). The pieces of living body data O1 to On are cohort data obtained from the persons U1 to Un at a certain timing, for example, in a periodic health examination.

The personal ID 301 is identification information for uniquely identifying a person. The intestinal bacterial flora 302 includes a plurality of intestinal bacteria 302-1, 302-2, ... (when the intestinal bacteria are not distinguished from one another, the intestinal bacteria is denoted by "302-x"). The value of the intestinal bacteria 302-x indicates the number of intestinal bacteria (or may be absence or presence of the bacteria). For example, the number of intestinal bacteria 302-1 (intestinal bacteria B1) corresponding to "U1" of the personal ID 301 is "b1(1)." The number of intestinal bacteria 302-2 (intestinal bacteria B2) corresponding to "U1" is "b2(1)."

The meal data 303 is the data indicating, for example, when, what, and how much the person has drunk and eaten. The basic data 304 is the basic data such as the body height, the body weight, and the body fat percentage of the person. The life style data 305 is data indicating, for example, the amount of drinking alcohol per week and the amount of smoking per week.

Figure 4:
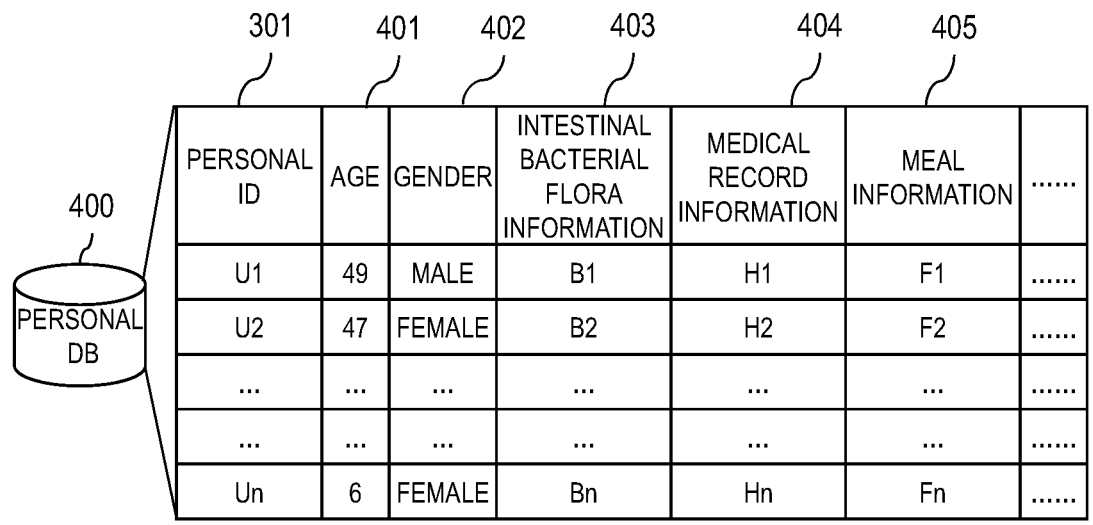
FIG. 4 is an explanatory diagram for illustrating an example of a personal DB.

FIG. 4 is an explanatory diagram for illustrating an example of a personal DB. A personal DB 400 includes, as fields, a personal ID 301, an age 401, a gender 402, intestinal bacterial flora information 403, medical record information 404, and meal information 405. A combination of values in the respective fields in one row forms an entry indicating attributes of each person. The age 401 is the number of years since the birth of a person. The gender 402 indicates whether the person is male or female.

The intestinal bacterial flora information 403 is information indicating the intestinal bacterial flora of the person. Specifically, for example, the intestinal bacterial flora information 403 may be an integrated value of the numbers of each intestinal bacteria 302-x of the intestinal bacterial flora 302 successively obtained from the living body DB 300, or may be the number obtained from the newest intestinal bacterial flora 302. The medical record information 404 is information indicating past diseases of the person. The meal information 405 is data indicating what and how much the person drinks and eats. Specifically, for example, the meal information 405 is an average value per unit period of an intake of foods included in the meal data successively obtained from the living body DB 300.

Figure 5:
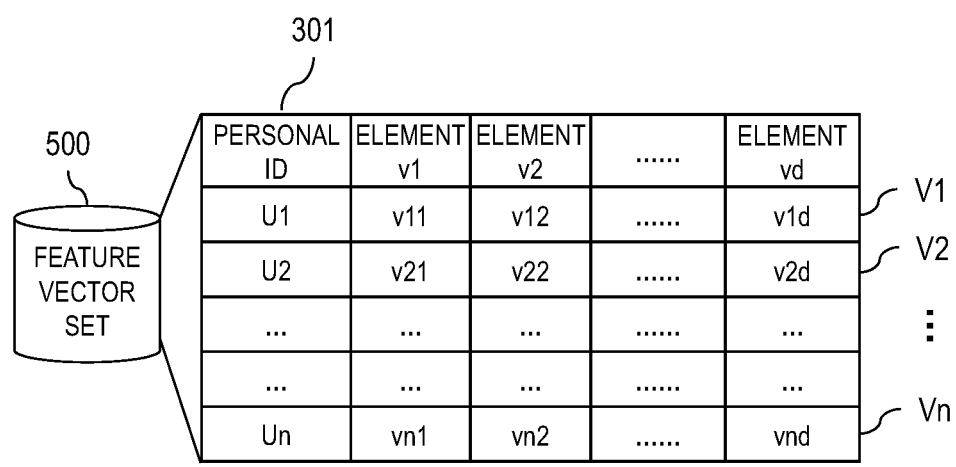
FIG. 5 is an explanatory diagram for illustrating an example of a feature vector set.

FIG. 5 is an explanatory diagram for illustrating an example of a feature vector set. A feature vector set 500 is a set of feature vectors V1 to Vn (when the feature vectors are not distinguished from one another, the feature vector is simply denoted by "V") corresponding to the respective persons. The feature vector V is an array of elements v1 to vd in d dimensions (d is an integer equal to or larger than 1). The elements v1 to vd are obtained by regularizing a part or the whole of the attributes of a person obtained from the living body DB 300. For example, the registration apparatus 200 may generate the feature vector set 500 from all of the attributes of the living body DB 300, or may generate the feature vector set 500 from the intestinal bacterial flora 302 of the living body DB 300.

Figure 6:
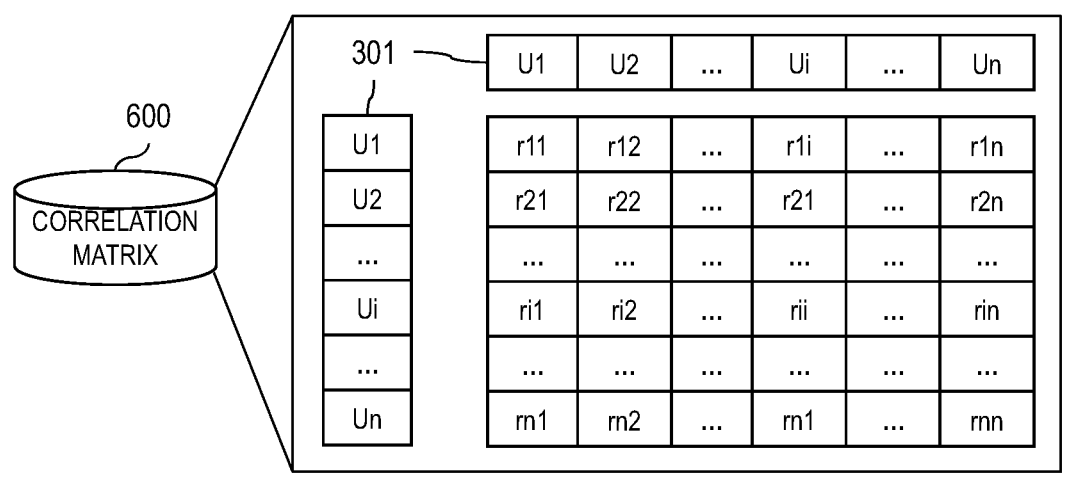
FIG. 6 is an explanatory diagram for illustrating an example of a correlation matrix.

FIG. 6 is an explanatory diagram for illustrating an example of a correlation matrix. A correlation matrix 600 is a set of correlations each between two persons calculated by the registration apparatus 200, and is a matrix having n rows and n columns. The correlation may be a correlation coefficient obtained from the feature vectors of the two persons, a Euclidean distance, or a cosine similarity.

<Functional Configuration Example of Registration Apparatus 200>

Figure 7:
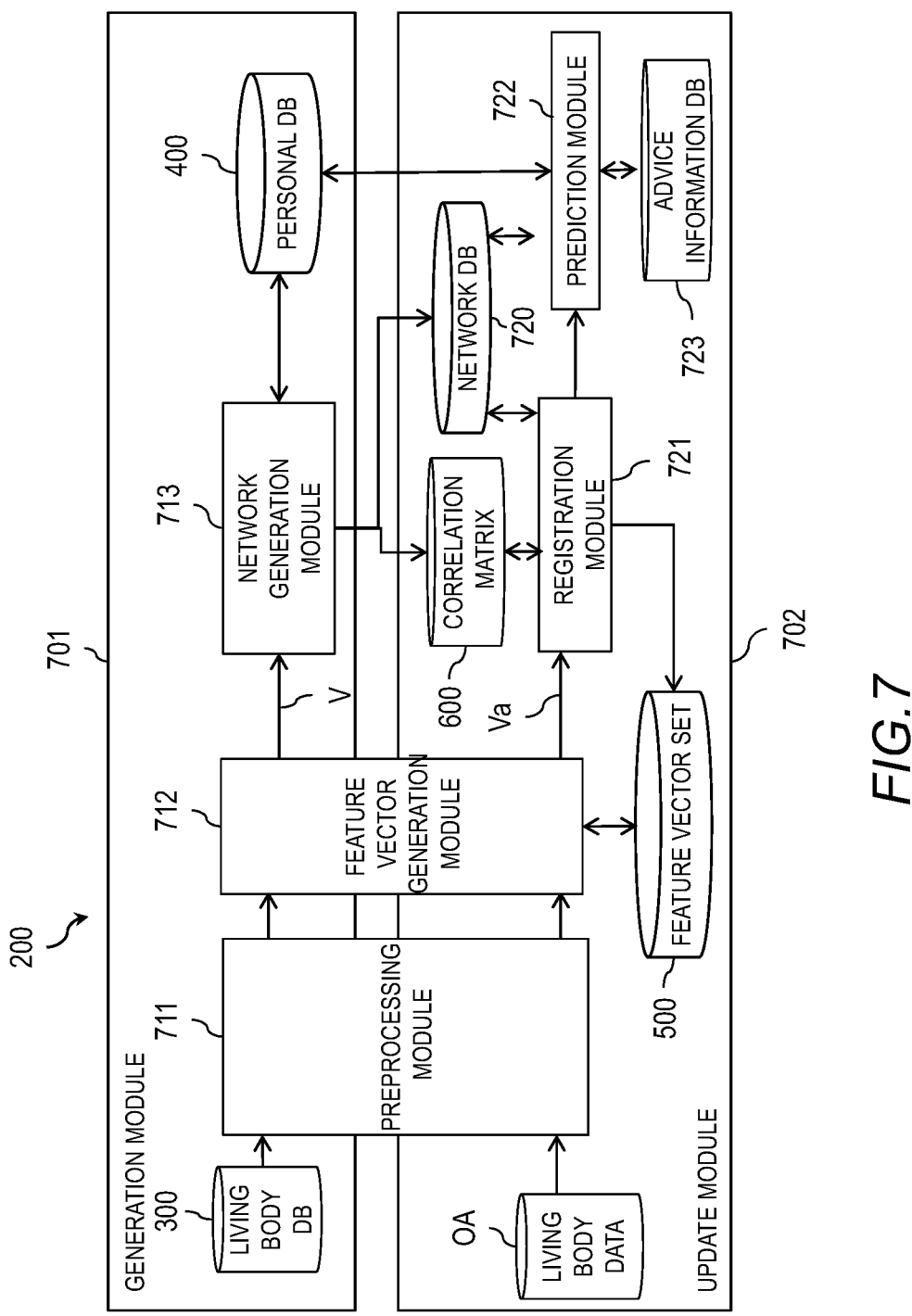
FIG. 7 is a block diagram for illustrating a functional configuration example of the registration apparatus.

FIG. 7 is a block diagram for illustrating a functional configuration example of the registration apparatus 200. The registration apparatus 200 is formed of a generation module 701 and an update module 702. The generation module 701 is configured to generate the network 101. Specifically, for example, the generation module 701 includes a preprocessing module 711, a feature vector generation module 712, and a network generation module 713. The update module 702 includes the preprocessing module 711, the feature vector generation module 712, a registration module 721, and a prediction module 722. Specifically, those modules are implemented by, for example, the processor 201 executing programs stored in the storage device 202 of FIG. 2. First, description is given of the generation module 701.

The preprocessing module 711 inputs the living body DB 300, and executes preprocessing in the generation module 701. The preprocessing module 711 narrows down the pieces of living body data O1 to On of the living body DB 300 in terms of the attributes of the fields. For example, when the preprocessing module 711 extracts the values of the intestinal bacterial flora 302 from the pieces of living body data O1 to On of the living body DB 300, the network 101 relating to the intestinal bacterial flora 302 is generated. When the preprocessing module 711 extracts the values of the life style data 305, the network 101 relating to the life style is generated. When the preprocessing module 711 extracts the values of the intestinal bacterial flora 302 and the values of the life style data 305, the network 101 relating to the intestinal bacterial flora and the life style is generated. When the preprocessing module 711 extracts respective values of a partial group of intestinal bacteria of the intestinal bacterial flora, the network 101 relating to the partial group of the intestinal bacteria is generated. How many attributes corresponding to what fields are to be applied may be specified by a user, or may be set in advance to the registration apparatus 200.

The feature vector generation module 712 generates the feature vectors V1 to Vn from the preprocessed pieces of living body data O1 to On of the living body DB 300 output from the preprocessing module 711. The respective elements of the pieces of living body data O1 to On have units different from one another, and hence the feature vector generation module 712 regularizes those elements, to thereby generate the feature vectors V1 to Vn.

The network generation module 713 generates the network 101 from the feature vector set 500, and stores the generated network 101 in a network DB 720. Specifically, for example, the network generation module 713 uses the feature vector set 500 to calculate and then hold the correlation matrix 600. Moreover, the network generation module 713 calculates a similarity S(Vi,Vj) for each feature vector Vi with a feature vector Vj (i≠j) as given by Expression (1).

$$S(V_i, V_j) = \frac{(V_i - m_i) \cdot (V_j - m_j)}{\|V_i - m_i\| \|V_j - m_j\|} \quad (1)$$

In Expression (1), mi represents an average value of the elements in the feature vector Vi, and mj represents an average value of the elements of the feature vector Vj. In the case of Expression (1), as the value of the similarity S(Vi,Vj) becomes smaller, the feature vectors Vi and Vj become more similar to each other. After that, the network generation module 713 arranges the nodes based on the similarity S(Vi,Vj) in accordance with a known dynamic model defined in the registration apparatus 200 in a feature space, and couples the nodes to one another with edges, to thereby generate the network 101.

It should be noted that each node of the network 101 includes the personal ID 301. Thus, when the network 101 is displayed, and the node is specified, an entry of the personal DB 400 corresponding to the personal ID 301 of the specified node is read out from the personal DB 400 and is displayed. In this case, as illustrated in FIG. 1, the registration apparatus 200 may refer to the intestinal bacterial flora 302 of the living body DB 300, and may display the nodes in different colors in accordance with the variety level so that the variety level can visually be recognized for each node.

It should be noted that, in at least one embodiment, the network generation module 713 generates the network 101, but the registration apparatus 200 may acquire the network 101 from an external computer. Description is now given of the update module 702.

The preprocessing module 711 inputs living body data OA on a new person in the update module 702, and executes the preprocessing. The living body data OA has the same combination of values in the fields as that of the pieces of living body data O1 to On. The preprocessing module 711 narrows down the living body data OA with respect to the attributes of the fields. The attributes that can be obtained through the narrowing-down are the attributes that have already been obtained through the narrowing-down by the generation module 701. For example, when the narrowing-down has been carried out with respect to the intestinal bacterial flora, the preprocessing module 711 can extract values of the intestinal bacterial flora 302 from the living body data OA. Attributes of which fields are to be applied are determined by the user.

The feature vector generation module 712 generates a feature vector Va from the preprocessed living body data OA output from the preprocessing module 711. The respective elements of the preprocessed living body data OA have units different from one another, and hence the feature vector generation module 712 regularizes those elements, to thereby generate the feature vector Va.

The registration module 712 uses the correlation matrix 600 to register the feature vector Va of the new person generated by the feature vector generation module 712 to the network 101, to thereby update the network 101 to a network 102. Details of the registration processing by the registration module 721 is described below with reference to FIG. 13. Regeneration of the network 102 from the existing node group and the new node, which is a case of the related art, can be avoided through the registration processing by the registration module 721. Thus, the computational load can be reduced, and a calculation period can thus be reduced.

The prediction module 722 refers to the personal DB 400, to thereby predict a state of the new person for the network 102 after the update. Specifically, for example, the prediction module 722 reads out, from the personal DB 400, entries of persons within the range of the circle 120 about the new node 110 of the new person as illustrated in part (B) of FIG. 1, and statistically processes the read entries of the persons, to thereby predict the state of the new person.

<Generation Processing Procedure>

Figure 8:
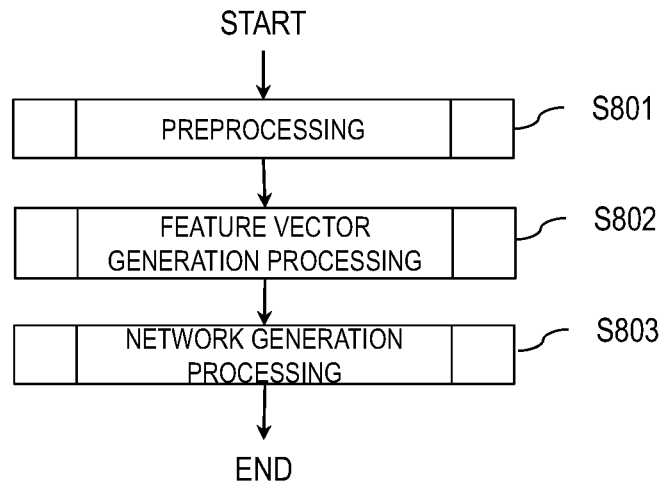
FIG. 8 is a flowchart for illustrating an example of a generation processing procedure by the generation module.

FIG. 8 is a flowchart for illustrating an example of a generation processing procedure by the generation module 701. First, the generation module 701 executes the preprocessing by the preprocessing module 711 (Step S801) and the feature vector generation processing (Step S802) by the feature vector generation module 712, to thereby obtain the feature vectors V. Moreover, the generation module 701 executes the network generation processing (Step S803) by the network generation module 713, to thereby generate the network 101, and stores the generated network 101 in the network DB 720.

Figure 9:
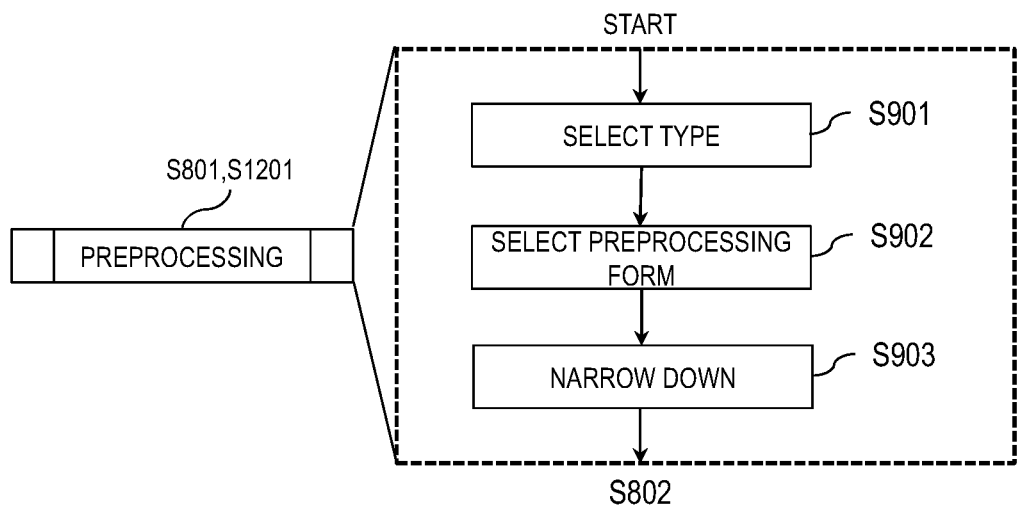
FIG. 9 is a flowchart for illustrating a detailed processing procedure example of the preprocessing by the preprocessing module.

FIG. 9 is a flowchart for illustrating a detailed processing procedure example of the preprocessing by the preprocessing module 711. The preprocessing module 711 selects a type of data to be preprocessed (Step S901), selects a form of the preprocessing for the living body data O having the type being selected (Step S902), and then narrows down the living body data O in accordance with the contents selected in Step S901 and Step S902 (Step S903).

Figure 10:
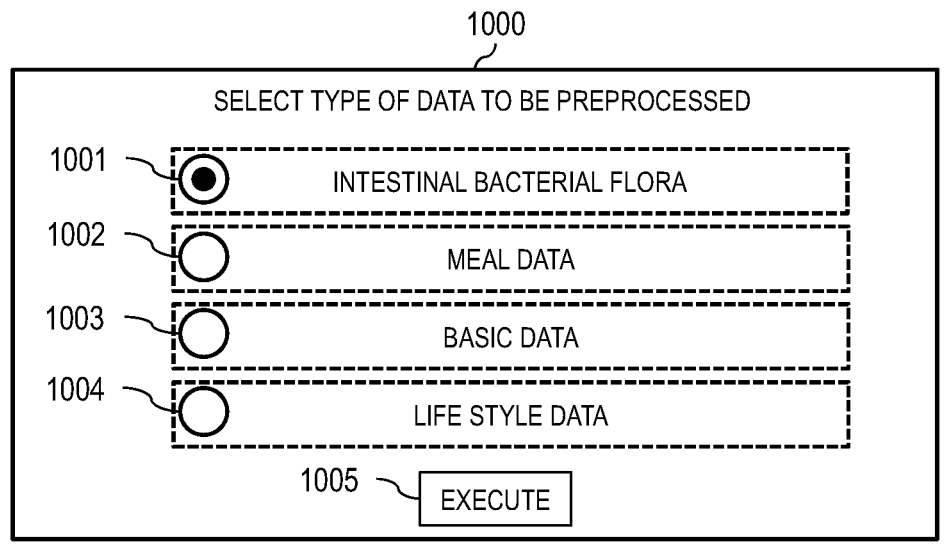
FIG. 10 is an explanatory diagram for illustrating an example of a type selection screen in the type selection (Step S901).

FIG. 10 is an explanatory diagram for illustrating an example of a type selection screen in the type selection (Step S901). The type selection screen 1000 includes, for example, type selection radio buttons 1001 to 1004, and an "execute" button 1005. In FIG. 10, the intestinal bacterial flora is selected with the type selection radio button 1001. Thus, when the "execute" button 1005 is pressed, the preprocessing module 711 extracts the values of the intestinal bacterial flora 302 from the pieces of living body data O1 to On of the living body DB 300. It should be noted that the user can select at least one of the type selection radio buttons 1001 to 1004.

Figure 11:
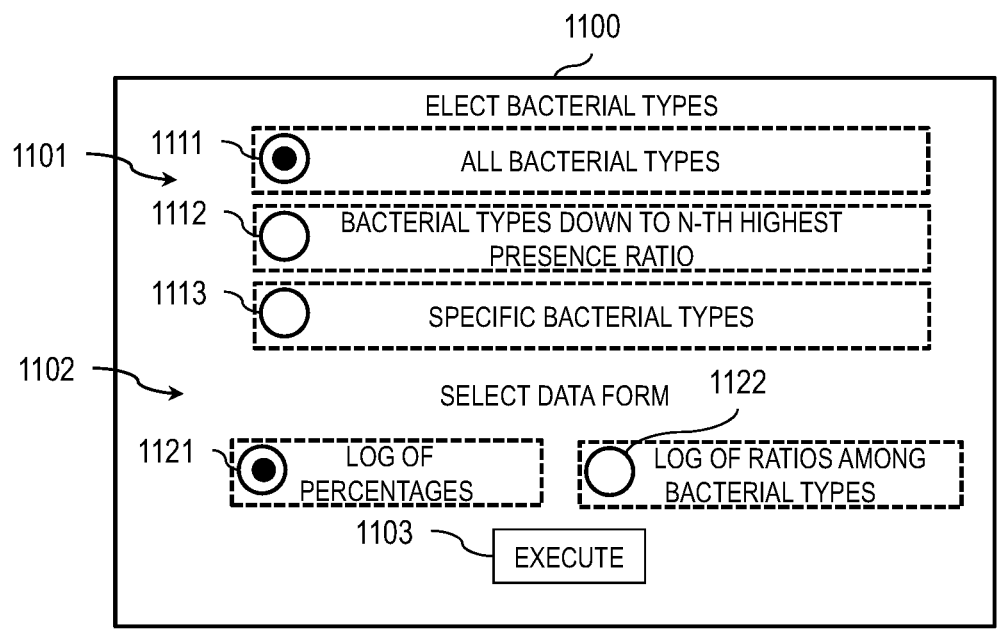
FIG. 11 is an explanatory diagram for illustrating an example of a preprocessing form selection screen in the preprocessing form selection (Step S902).

FIG. 11 is an explanatory diagram for illustrating an example of a preprocessing form selection screen in the preprocessing form selection (Step S902). In FIG. 11, there is illustrated a preprocessing form selection screen 1100 displayed when the intestinal bacterial flora has been selected in the type selection screen 1000. The preprocessing form selection screen 1100 includes a bacterial type selection area 1101, a data form selection area 1102, and an "execute" button 1103.

The bacterial type selection area 1101 includes a first bacterial type selection radio button 1111, a second bacterial type selection radio button 1112, and a third bacterial type selection radio button 1113. The first bacterial type selection radio button 1111 is a radio button for selecting all bacterial types (B1, B2, . . . ). The second bacterial type selection radio button 1112 is a radio button for selecting bacterial types down to the N-th highest presence ratio. The presence ratio is an index value indicating the number of bacterial types existing in a person, and has the total number of bacterial types as the denominator and the number of bacterial types held by the person as the numerator.

The third bacterial type selection radio button 1113 is a radio button for selecting specific bacterial types. The specific bacterial types may be set in advance, or may be selected from a selection screen (not shown) displaying a list of specific bacterial types when the third bacterial type selection radio button 1113 is selected.

The data form selection area 1102 includes a first data form selection radio button 1121 and a second data form selection radio button 1122. The first data form selection radio button 1121 is a radio button for converting the living body data O to a log of percentages. The log of percentages is an index value indicating a percentage of bacterial types held by each person in the selected bacterial types. Specifically, for example, when the number of the selected bacterial types is 100 including the intestinal bacteria B1 to B100, an intestinal bacteria held by a certain person is represented as 1%, and an intestinal bacteria not held by the person is represented as 0%.

The second data form selection radio button 1122 is a radio button for converting the living body data to a log of ratios among the bacterial types. The log of the ratios among the bacterial types are ratios obtained when the numbers of respective bacterial types are compared with one another. Specifically, for example, when the total number of bacteria of the selected bacterial types including the intestinal bacteria B1 to B100 is X, and the numbers of the respective intestinal bacteria B1 to B100 are x1 to x100, respectively, the log of the ratios among the bacterial types includes x1/X for the intestinal bacteria B1, x2/X for the intestinal bacteria B2, . . . , and x100/X for the intestinal bacteria B100.

The "execute" button 1103 is a button for narrowing down the pieces of living body data O1 to On in accordance with the selection results of FIG. 10 and FIG. 11.

Figure 12:
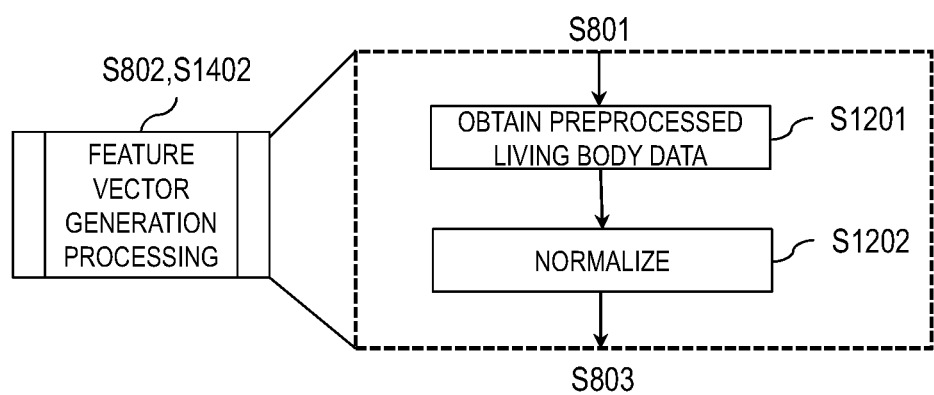
FIG. 12 is a flowchart for illustrating a detailed processing procedure example of the feature vector generation processing by the feature vector generation module.

FIG. 12 is a flowchart for illustrating a detailed processing procedure example of the feature vector generation processing by the feature vector generation module 712. The feature vector generation module 712 obtains the living body data O after the preprocessing of Step S801 (Step S1201). After that, the feature vector generation module 712 regularizes the obtained living body data O after the preprocessing of Step S801 (Step S1202). As a result, the feature vectors V1 to Vn are generated.

Figure 13:
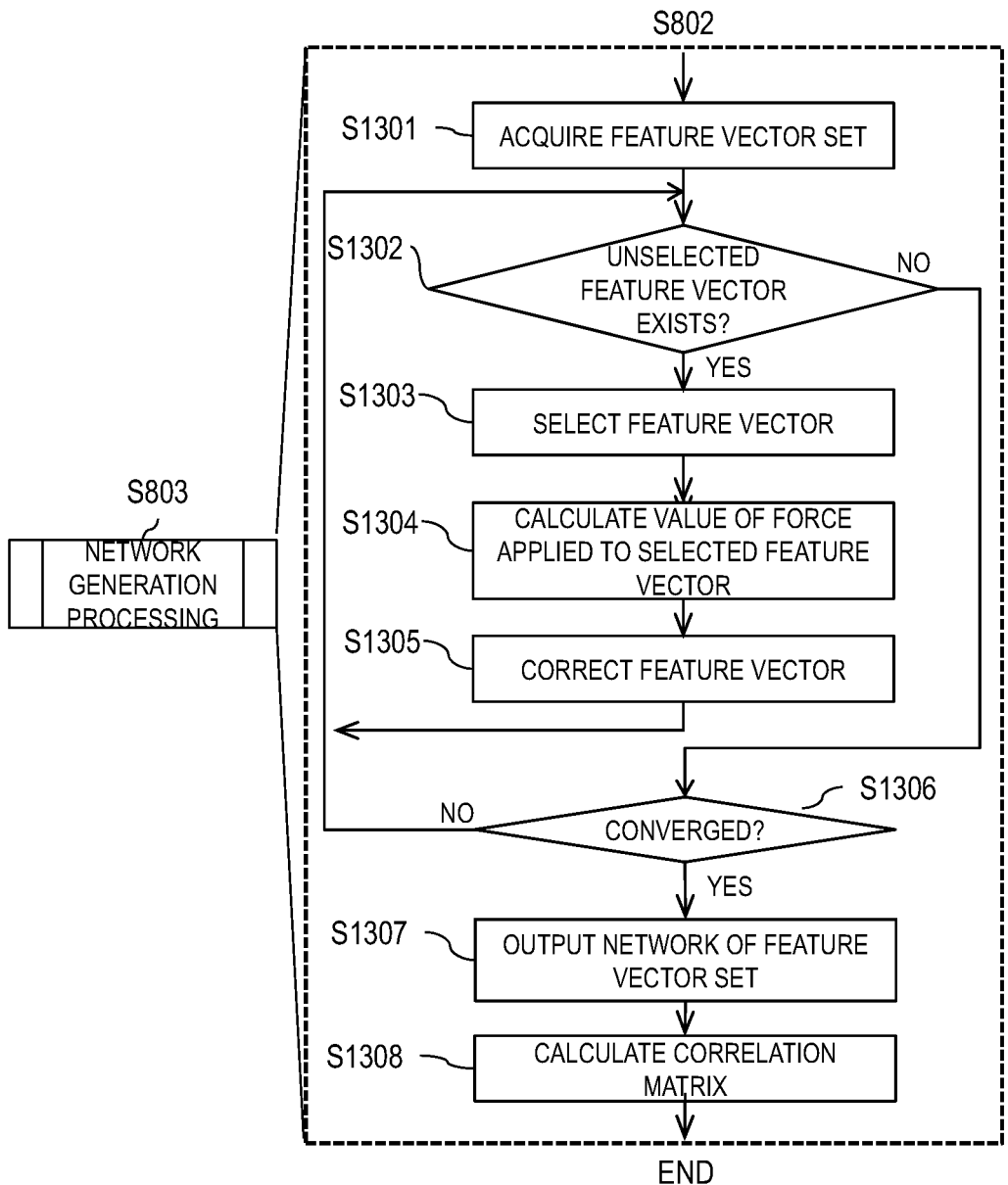
FIG. 13 is a flowchart for illustrating a detailed processing procedure example of the network generation processing by the network generation module.

FIG. 13 is a flowchart for illustrating a detailed processing procedure example of the network generation processing by the network generation module 713. The network generation module 713 obtains the feature vector set 500 (Step S1301), and determines whether or not an unselected feature vector exists (Step S1302). When unselected vectors exist (Yes in Step S1302), the network generation module 713 selects one of the unselected feature vectors (Step S1303).

The network generation module 713 calculates a value of a force from another feature vector Vj to the selected feature vector Vi based on the dynamic model (Step S1304), and proceeds to Step S1305. The value of the force is, for example, a value corresponding to a sum of an attractive force "fa" and a repulsive force "fr" acting between the selected feature vector Vi and the another feature vector Vj. The attractive force "fa" is calculated as given by Expression (2). The repulsive force "fr" is calculated as given by Expression (3).

$$fa(V_i, V_j) = \frac{S(V_i, V_j) \cdot \|V_i - V_j\|}{k} \quad (2)$$

$$fr(V_i, V_j) = -\frac{Ck^2}{\|V_i - V_j\|} \quad (3)$$

In Expression (2) and Expression (3), ‖Vi-Vj‖ represents the 2-norm (distance) between Vi and Vj. Moreover, C and "k" are adjustable parameters, and constants determined in advance before the calculation.

The attractive force "fa" is defined based on the similarity S(Vi,Vj) between Vi and Vj so as to be in proportion thereto. The attractive force "fa" is based on the distance between Vi and Vj, and becomes larger as the distance becomes longer.

The repulsive force "fr" between the Vi and Vj is based on the distance between Vi and Vj, and becomes larger as the distance becomes shorter. The repulsive force "fr" is based on the reciprocal of the distance between Vi and Vj, to thereby allow avoidance of collision between Vi and V. Forces from all of the other feature vectors Vj existing in the feature space are applied to the one feature vector Vi in the feature space. The attractive force "fa" and the repulsive force "fr" act between each of all pairs of the feature vectors in the feature space.

Moreover, in Step S1304, the network generation module 713 calculates energy of the feature space. A force f(Vi) acting on the selected feature vector Vi 415 is given by Expression (4) as a sum of the attractive forces "fa" and the repulsive forces "fr" defined as described above.

$$f(V_i) = \Sigma fa(V_i, V_j) v(V_j, V_i) + \Sigma fr(V_i, V_j) v(V_j, V_i) \quad (4)$$

In Expression (4), the sum is calculated for all Vj other than Vi. Moreover, v(Vj,Vi) is a unit vector directed from Vi to Vj, and is defined by Expression (5).

$$v(V_i, V_j) = \frac{V_j - V_i}{\|V_j - V_i\|} \quad (5)$$

Overall potential energy E of the feature space is given by Expression (6) through use of the total forces f(Vi).

$$E = \Sigma \|f(V_i)\|^2 \quad (6)$$

In Expression (6), the sum is calculated for all of the feature vectors V, and ‖f(Vi)‖ indicates the magnitude of the vector f(Vi). As given by Expression (6), the potential energy E is determined from the absolute values of the total forces f(Vi) of the feature vectors Vi, and the sum of the absolute values of the forces represents the potential energy E.

Next, the network generation module 713 corrects the selected feature vector Vi (Step S1305), and returns to Step S1302. Specifically, for example, the network generation module 713 corrects the selected feature vector Vi in accordance with the attractive forces and the repulsive forces thereof such that a node representing the selected feature vector Vi does not overlap nodes representing the other feature vectors Vj in the feature space in which the network 101 is to be arranged. The energy based on all of the feature vectors V is in proportion to the attractive forces and the repulsive forces. As a difference between the energy for the current time and energy immediately before becomes larger, the node represented by the selected feature vector Vi moves more in the feature space. As the difference becomes smaller, the node moves less in the feature space.

Specifically, for example, the network generation module 713 uses Expression (7) to correct the arrangement position of the selected feature vector Vi.

$$V_i \leftarrow V_i + \text{step} \times \frac{f(V_i)}{\|f(V_i)\|} \quad (7)$$

In Expression (7), "step" represents a parameter for adjusting a width of the correction, and is a constant determined in advance in this example. The feature vector V indicates a position (coordinates) in the feature space, and hence the correction of the feature vector means correction of the position of the feature vector V. Expression (7) is an example of the correction of the feature vector V, and the feature vector may be corrected in accordance with another numerical expression. A correction amount of the feature vector V may be in proportion to the absolute value of the force applied to the feature vector V.

After that, when an unselected feature vectors V does not exist in Step S1302 (No in Step S1302), the network generation module 713 determines whether or not each of the feature vectors V has converged (Step S1306).

Specifically, for example, it is assumed that all of the feature vectors V after the correction in the loop for the current time are represented by {Vi}, and all of the feature vectors V immediately before the correction in the loop for the current time are represented by {Vi°}. The network generation module 713 compares {Vi°} and {Vi} with each other, to thereby determine the convergence based on a correction amount thereof.

For example, the correction amount can be calculated through use of Σ‖Vi-Vi°‖. When the correction amount is larger than a predetermined threshold value, the network generation module 713 determines that each of the feature vectors has not converged (No in Step S1306), returns to Step S1302 to continue the calculation. Meanwhile, when the correction amount is equal to or smaller than the threshold value, the network generation module 713 determines that each of the feature vectors V has converged (Yes in Step S1306).

As described above, the network generation module 713 rearranges the feature vectors V such that the potential energy E is within a predetermined range from the minimum value. The threshold value is 0 or a positive numerical value set in advance. The threshold value 0 means that the converged state has the minimum potential energy (0).

It should be noted that the correction amount may be represented by the potential energy E (the sum of the absolute values of the forces). The network generation module 713 may compare a difference between the potential energy E before the correction and the potential energy E after the correction with a threshold value, to thereby determine the convergence. Moreover, the network generation module 713 may determine that each of the feature vectors V has converged when the potential energy E is equal to or smaller than the threshold value.

When each of the feature vectors V has converged (Yes in Step S1306), the network generation module 713 outputs the network 101 formed of the feature vector set 500 (Step S1307). Moreover, the network generation module 713 calculates a correlation matrix 600 (referred to as "RN") representing correlation among the n existing persons (Step S1308). The correlation matrix RN is represented by a matrix having n rows and n columns.

<Update Processing Procedure>

Figure 14:
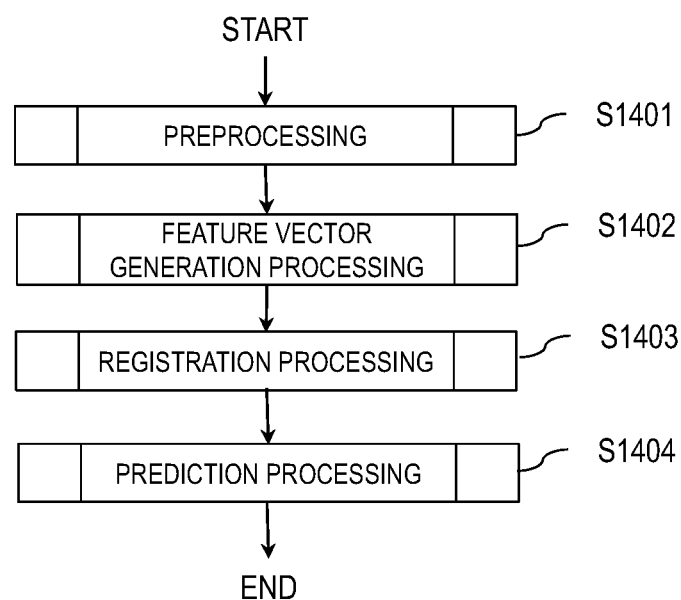
FIG. 14 is a flowchart for illustrating an example of an update processing procedure by the update module.

FIG. 14 is a flowchart for illustrating an example of an update processing procedure by the update module 702. First, as with the processing of FIG. 8, the update module 702 executes the preprocessing by the preprocessing module 711 (Step S1401) and the feature vector generation processing (Step S1402) by the feature vector generation module 712, to thereby obtain the feature vector Va. The preprocessing (Step S1401) is the same processing as the preprocessing (Step S801) except for a point that the data subjected to the preprocessing is the living body data OA on the new person. The feature vector generation processing (Step S1402) is also the same processing as the feature vector generation processing (Step S802) except for a point that the vector to be generated is the feature vector Va of the new person.

Moreover, the update module 702 executes the registration processing (Step S1403) for the new node by the registration module 721, to thereby add the new node 110 to the network 101. Further, the update module 702 executes the prediction processing by the prediction module 722 (Step S1404), to thereby predict the state of the person corresponding to the new node 110, and outputs a prediction result.

<Registration Processing Procedure>

Figure 15:
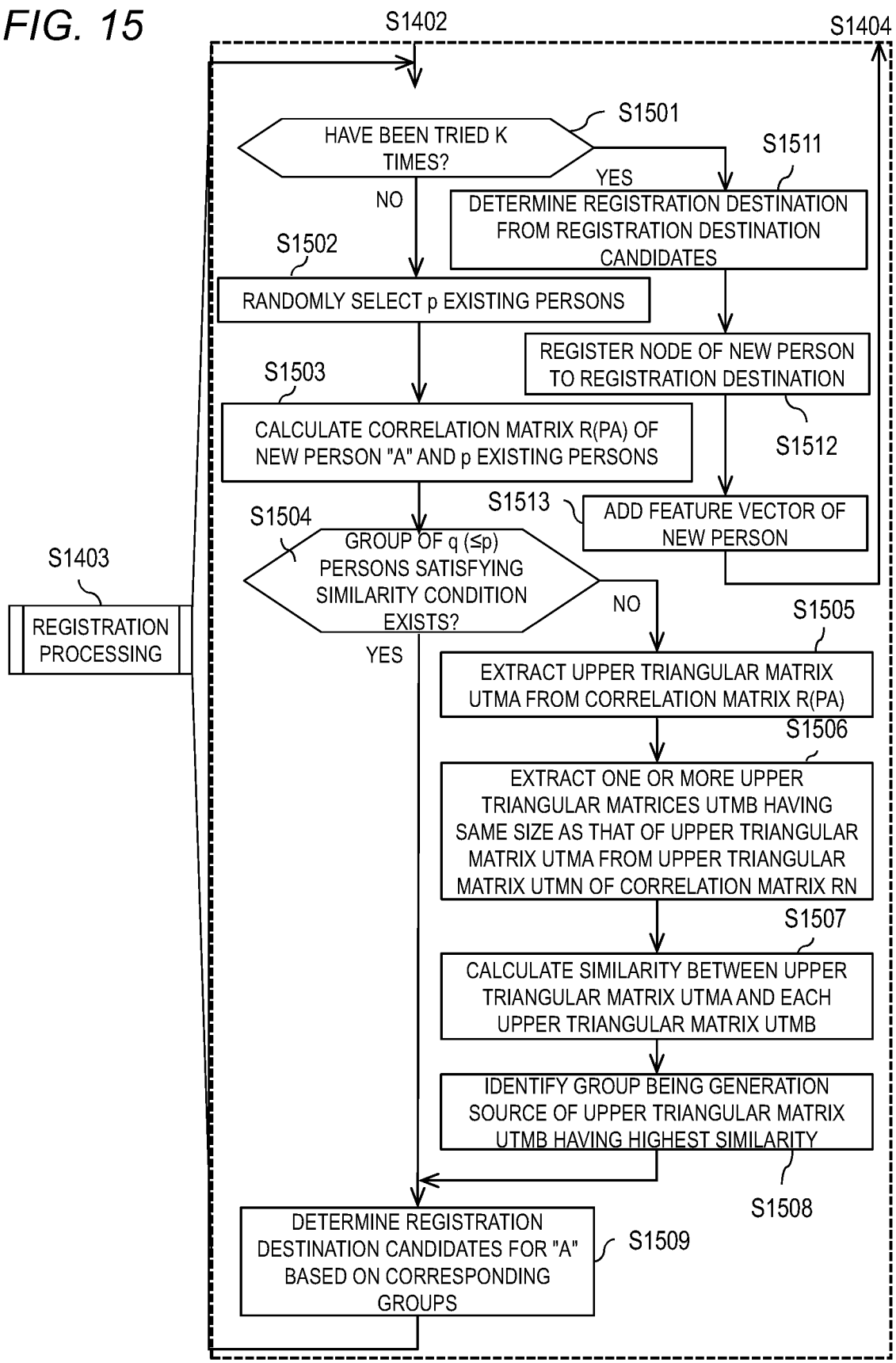
FIG. 15 is a flowchart for illustrating a detailed processing procedure example of the registration processing (Step S1403) of FIG. 14.
Figure 16:
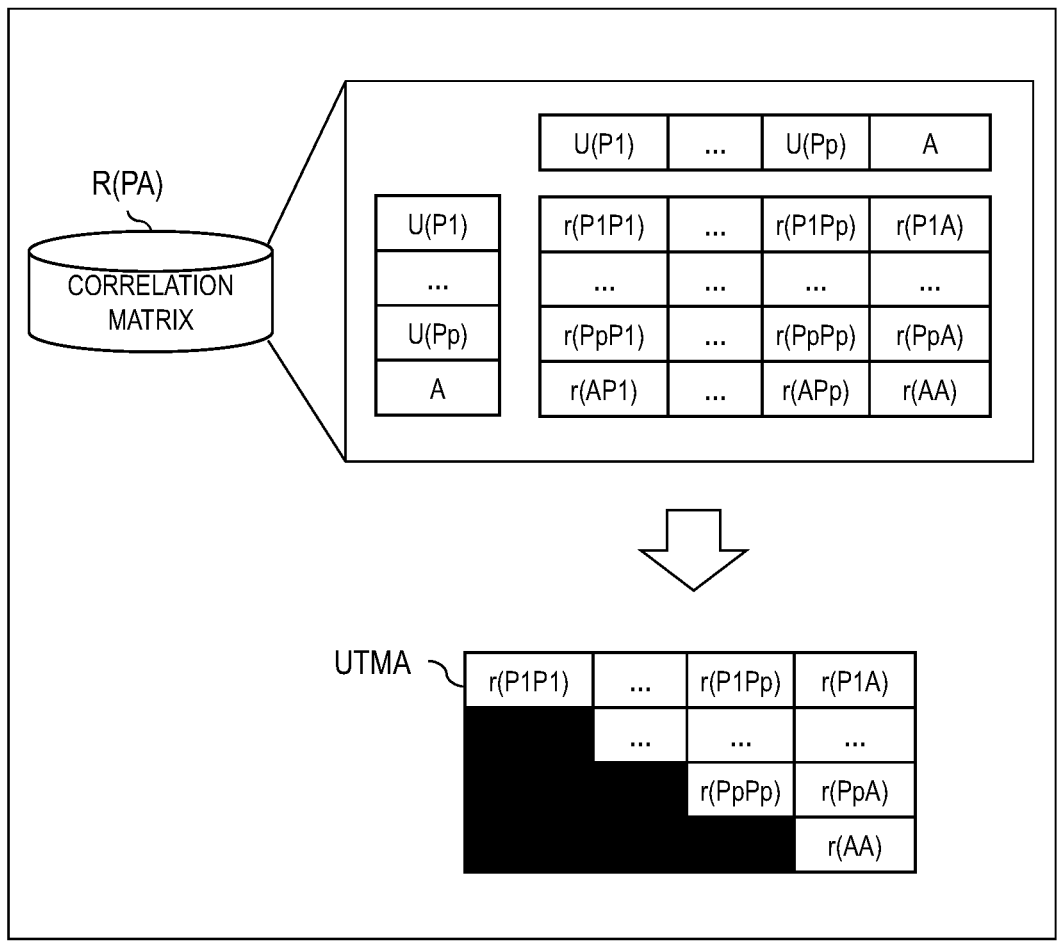
FIG. 16 is an explanatory diagram for illustrating an extraction example 1 of an upper triangular matrix.
Figure 17:
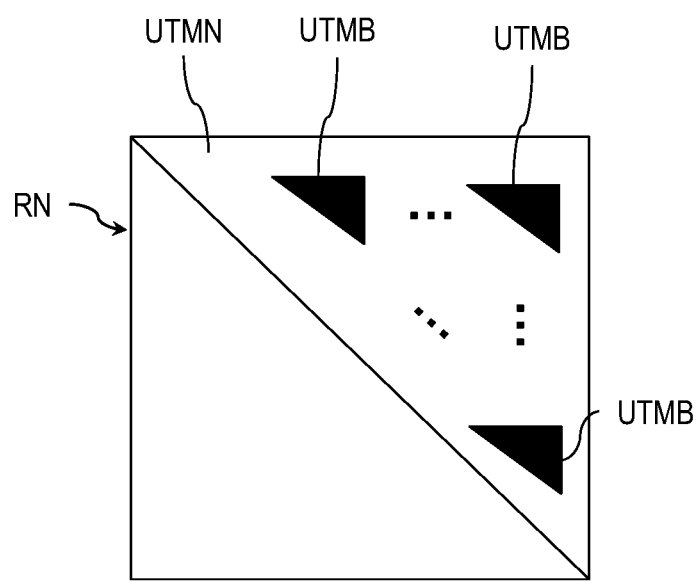
FIG. 17 is an explanatory diagram for illustrating an extraction example 2 of upper triangular matrices.

FIG. 15 is a flowchart for illustrating a detailed processing procedure example of the registration processing (Step S1403) of FIG. 14. FIG. 16 is an explanatory diagram for illustrating an extraction example 1 of an upper triangular matrix. FIG. 17 is an explanatory diagram for illustrating an extraction example 2 of upper triangular matrices. First, the registration module 721 determines whether or not a trial has been made K(≥1) times (Step S1501). When the trial has not been made the K times (No in Step S1501), the registration module 721 randomly selects p (<n) existing persons (Step S1502). As a result, compared with a case in which the n persons are used for re-clustering, a calculation amount becomes p/n times.

After that, a correlation matrix R(PA) of the new person A and p existing persons is calculated (Step S1503). The correlation matrix R(PA) is represented by a matrix having (p+1) rows and (p+1) columns. It should be noted that Step S1503 may be executed before Step S1505 when the determination of "No" is made in Step S1504.

After that, the registration module 721 determines whether or not a group Gq including q (p) persons satisfying a predetermined similarity condition exists in a group Gp including the existing p persons (Step S1504). The variables p and q are values set in advance. Specifically, for example, the registration module 721 uses Expression (1) to exhaustively calculate similarities between the existing persons in the group Gq. When there is satisfied a condition, as the predetermined similarity condition, that a sum of differences each between the respective similarities is within a threshold value, existence of the group Gq is determined.

When the existence of the group Gq is determined (Yes in Step S1504), the registration module proceeds to Step S1509. When the existence of the group Gq is not determined (No in Step S1504), the registration module 721 extracts an upper triangular matrix UTMA from the correlation matrix R(PA) calculated in Step S1503 as illustrated in FIG. 16 (Step S1505). After that, as illustrated in FIG. 17, the registration module 721 extracts, from the upper triangular matrix UTMN of the correlation matrix RN calculated in Step S1308, one or more upper triangle matrices UTMB having the same size as that of the upper triangular matrix UTMA (Step S1506).

After that, the registration module 721 calculates a similarity between the upper triangular matrix UTMA and each triangle matrix UTMB (Step S1507). This similarity is defined by, for example, a reciprocal of a Euclidean distance between the upper triangular matrix UTMA and the upper triangular matrix UTMB. The registration module 721 identifies a group being a generation source of an upper triangular matrix UTMB having the highest similarity (Step S1508), and proceeds to Step S1509. Specifically, for example, the registration module 721 identifies, for each element of the upper triangular matrix UTMB having the highest similarity, two persons being a source of a correlation value forming the element, to thereby form a group of the identified persons as a group Gr being the generation source.

In Step S1509, the registration module 721 determines registration destination candidates of the new person A based on the groups Gq or the group Gr (Step S1509). Specifically, for example, when one or more groups Gq are determined, the registration module 721 determines each group Gq as the registration destination candidate of the new person A. When the group Gr is identified, the registration module 721 determines the group Gr as the registration destination candidate of the new person A. After that, the registration module 721 returns to Step S1501.

In Step S1501, when the trial has been made the K times (Yes in Step S1501), the registration module 721 determines a registration destination from the registration destination candidates (Step S1511). Specifically, for example, among the K times of the trials, the members of the group Gp are different from one another. Thus, the registration module 721 sums, for the group Gp having the same members, the number of groups Gq and the number of groups Gr.

After that, the registration module 721 selects the registration destination from the groups, which are any one of the groups Gq and the groups Gr, and have a larger number of groups.

For example, when the number of groups Gq is "5" and the number of groups Gr is "3", the registration destination is determined from the groups Gq including the five groups (referred to as "Gq1" to "Gq5", and it is assumed that Gq1 has the smallest number of members and Gq5 has the largest number of members). In this case, the registration module 721 may randomly determine one of the groups Gq1 to Gq5 as the registration destination, or may determine the group Gq5 having the largest number q of members as the registration destination.

Moreover, in the case of the groups Gr, any groups Gr have the same number of members, and the registration module 721 may thus determine the group Gr having the highest similarity as the registration destination. For example, when the number of groups Gq is "2" and the number of groups Gr is "6", the registration destination is determined from the groups Gr including the six groups (referred to as "Gq1" to "Gq6", and it is assumed that Gr1 has the lowest similarity (least similar) and Gr6 has the highest similarity (most similar)). In this case, the registration module 721 may randomly determine one of the groups Gr1 to Gr6 as the registration destination, or may determine the group Gr6 having the highest similarity.

It should be noted that, in addition to the determination of the registration destination described above, the registration module 721 may display the registration destination candidates to allow the user to select the registration destination candidate, and may determine the selected registration destination candidate as the registration destination.

After that, the registration module 721 registers the node representing the feature vector of the new person to the determined registration destination (Step S1512). Specifically, for example, the registration module 721 arranges the new node in a vicinity of a node that belongs to the group of the nodes being the registration destination and has the highest correlation. For example, the registration module 721 arranges the new node in the vicinity of the node having the largest correlation coefficient based on correlation coefficients each between the new node and each node that belongs to the node group being the registration destination, and couples the new node to each node of the node group being the registration destination to each other with an edge.

Moreover, the registration module 721 arranges the new node in a vicinity of the node (for example, a position apart from the node by the Euclidean distance) having the highest similarity based on the similarity (for example, the reciprocal of the Euclidean distance) between the new node and each node of the node group being the registration destination. After that, the registration module 721 registers the living body data OA on the new person to the living body DB 300, and adds the feature vector Va of the new person to the feature vector set 500 (Step S1513). As a result, the registration processing (Step 1403) is finished, and the update module 702 proceeds to the prediction processing (Step S1404). It should be noted that, with reference to FIG. 15 to FIG. 17, description has been given of the example in which the upper triangular matrices are extracted, but the lower triangle matrices may be extracted.

<Prediction Processing Procedure>

Figure 18:
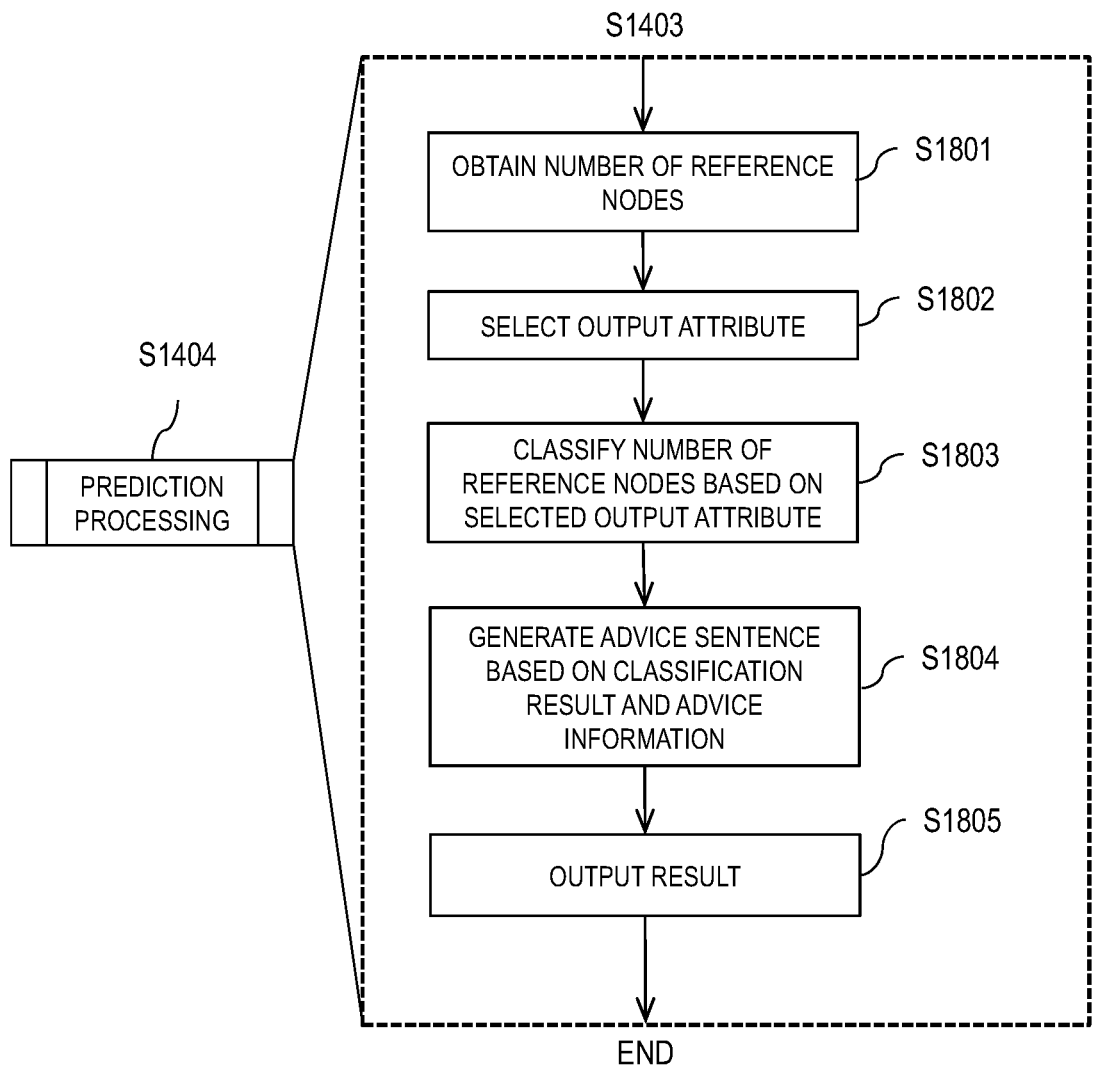
FIG. 18 is a flowchart for illustrating a detailed processing procedure example of the prediction processing (Step S1404) of FIG. 14.

FIG. 18 is a flowchart for illustrating a detailed processing procedure example of the prediction processing (Step S1404) of FIG. 14. First, the prediction module 722 obtains the number of reference nodes (Step S1801). The number of reference nodes is the number of nodes centered around the new node 110. The number of reference nodes may be set in advance, or may be a value input by the user. The number of reference nodes is the number of nodes enclosed by the circle 120 about the new node 110. In other words, the size of the circle 120 is determined based on the number of reference nodes. It should be noted that, instead of nodes determined based on the number of reference nodes, nodes within a similarity range (for example, within a predetermined Euclidean distance) centered around the new node 110 may be obtained as the reference nodes. After that, the prediction module 722 selects an output attribute (Step S1802).

Figure 19:
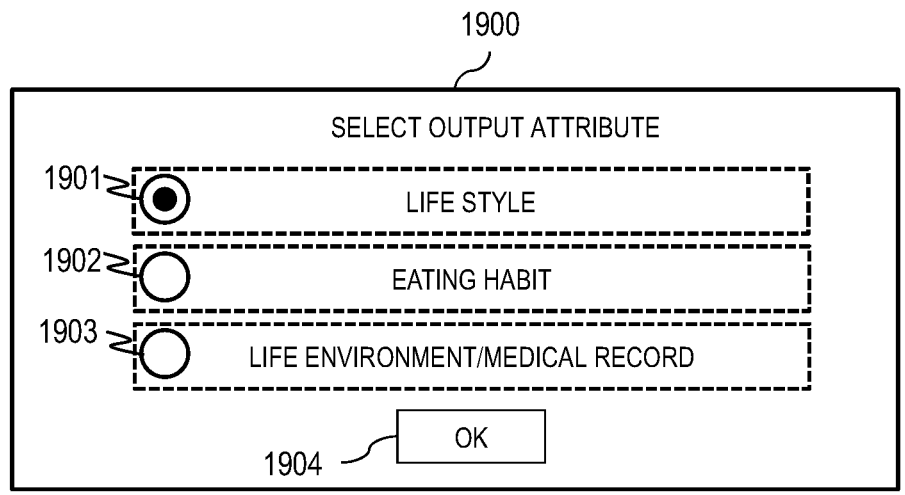
FIG. 19 is an explanatory diagram for illustrating an example of an output attribute selection screen.

FIG. 19 is an explanatory diagram for illustrating an example of an output attribute selection screen. An output attribute selection screen 1900 includes a life style radio button 1901, an eating habit radio button 1902, a life environment/medical record radio button 1903, and an OK button 1904. The life style radio button 1901 is a radio button for extracting values of fields relating to the life style from entries of the personal DB 400 associated through the same personal IDs 301 with the living body data O within the circle 120.

The eating habit radio button 1902 is a radio button for extracting values of fields relating to the eating habit from entries of the personal DB 400 associated through the same personal IDs 301 with the living body data O within the circle 120. The life environment/medical record radio button 1903 is a radio button for extracting values of fields relating to the life environment/medical from entries of the personal DB 400 associated through the same personal IDs 301 with the living body data O within the circle 120. A plurality of buttons can simultaneously be selected from among the life style radio button 1901 to the life environment/medical record radio button 1903. The OK button 1904 is a button for transmitting information selected through pressing of the life style radio button 1901 to the life environment/medical record radio button 1903.

Referring back to FIG. 18, the prediction module 722 classifies the number of reference nodes based on the selected output attribute (Step S1803). After that, the prediction module 722 generates an advice sentence based on the classification result obtained in Step S1803 and advice information of an advice information DB 723 (Step S1804).

After that, the prediction module 722 outputs a result screen including the classification result and the generated advice sentence (Step S1805), and finishes the prediction processing (Step S1404).

Figure 20:
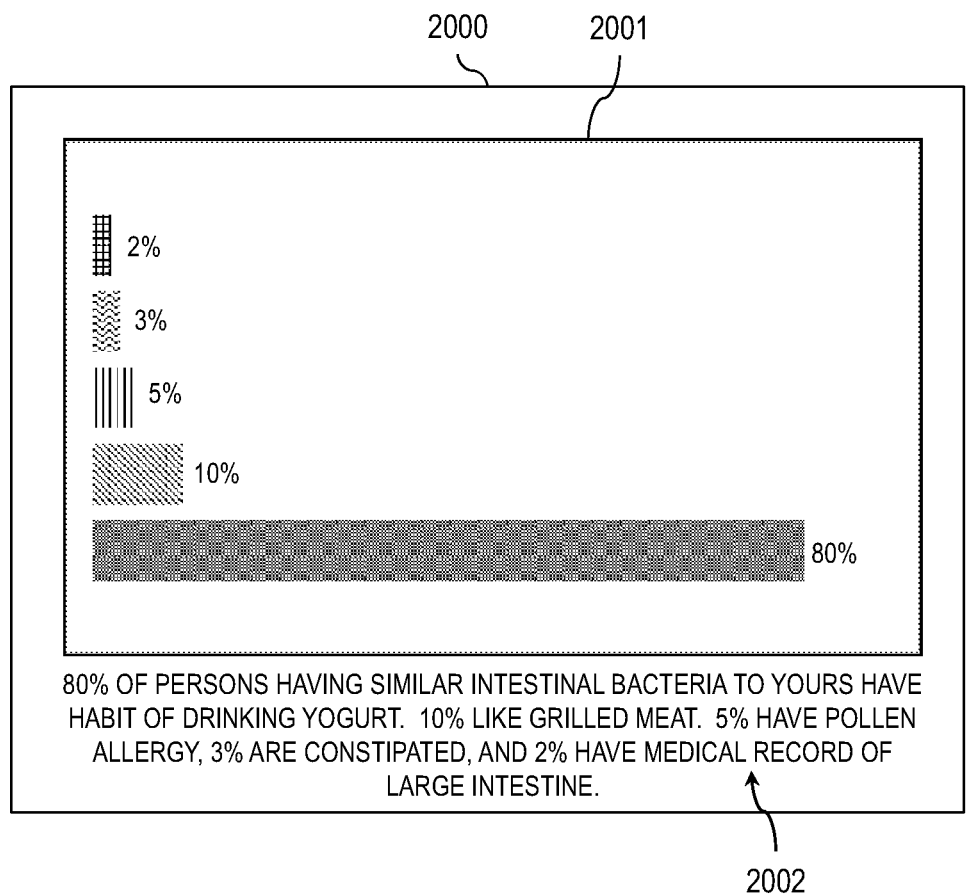
FIG. 20 is an explanatory diagram for illustrating an example of the result screen which is output in Step S1805.

FIG. 20 is an explanatory diagram for illustrating an example of the result screen which is output in Step S1805. A result screen 2000 includes a classification result 2001 and an advice sentence 2002. The classification result 2001 is, for example, a histogram indicating numbers of persons. For example, of the number of reference nodes, 2% of the existing persons have a medical record of the large intestine (selected by the life environment/medical record radio button 1903), 3% of the existing persons are constipated (selected by the life style radio button 1901), 5% of the existing persons have pollen allergy (selected by the life environment/medical record radio button 1903), 10% of the existing persons like grilled meat (selected by the eating habit radio button 1902), and 80% of the existing persons have a habit of drinking yogurt (selected by the eating habit radio button 1902).

Moreover, the new person represented by the new node 110 corresponds to "you" of the advice sentence 2002. Further, the existing persons represented by as many nodes as the number of reference nodes correspond to "persons having similar intestinal bacteria to yours" of the advice sentence 2002.

Moreover, remainders of the sentence are strings of the sentences formed from the classification result 2001.

As described above, according to the at least one embodiment, compared with a case in which the network 102 is newly generated, the computational load can be reduced, and the calculation period can thus be reduced. The registration apparatus can execute various predictions for the person corresponding to the new node 110.

Moreover, the registration apparatus 200 according to the at least one embodiment may be configured as described in Items (1) to (6).

(1) There is provided a registration apparatus 200 including a processor 201 configured to execute a program, and a storage device 202 configured to store the program, and the registration apparatus 200 is configured to access a network 101 formed of a set of first nodes and first edges, the first nodes each representing a first feature vector (V1 to Vn) including a plurality of elements, the first edges each coupling two first nodes representing two first feature vectors to each other based on two first feature vectors. The processor 201 is configured to execute: obtaining processing of obtaining a second feature vector (Step S1401, Step S1402); and registration processing of registering a second node (new node 110) representing the second feature vector (Va) obtained in the obtaining processing to the network 101 based on a similarity relationship among third feature vectors in a set of third feature vectors included in the set of first feature vectors, and coupling the second node and a third node representing the third feature vector to each other with a second edge (Step S1403), the number of third feature vectors being smaller than the number of first feature vectors.

With this configuration, the computational load can be reduced by using the set of third feature vectors smaller in number than the first feature vectors in the set of first feature vectors. Thus, a calculation period for updating the network 101 to the network 102 can be reduced. In other words, as the number p ($<n$) of the third feature vectors decreases, the computational load is reduced, and the calculation period is thus reduced. Moreover, as the number p ($<n$) of the third feature vectors increases, the second node (new node 110) can be arranged at a more appropriate position.

(2) Further, in Item (1), the processor 201 is configured to execute: determination processing of determining whether a first similar group Gq of specific third feature vectors exists in the set of third feature vectors, the specific third feature vectors satisfying a predetermined similarity condition (Step S1504); and determination processing of determining, as a registration destination of the second node, a position in the network which is based on the specific third feature vectors included in the first similar group Gq when the first 710 similar group Gq is determined to exist through the determination processing (Step S1509), and in the registration processing, the processor 201 is configured to register the second node to the registration destination determined through the determination processing, and couple the second node and a third node representing the specific third feature vector to each other with the second edge.

With this configuration, the determination of the registration destination of the second node (new node 110) can be facilitated.

(3) Further, in Item (2), the registration apparatus 200 is configured to access first correlation data (upper triangular matrix UTMN of correlation matrix RN), which represents correlation between each pair of first feature vectors in the network 101, the processor 201 is configured to execute correlation data calculation processing of calculating second correlation data (upper triangular matrix UTMA) indicating correlation between the second feature vector and each of the third feature vectors and correlation between each pair of third feature vectors (Step S1503, Step S1505), in the determination processing, the processor is configured to execute: extraction processing of extracting, when the first similar group Gq is determined not to exist through the determination processing, from the first correlation data (upper triangular matrix UTMN of correlation matrix RN), third correlation data (upper triangular matrix UTMB) having the same size as the size of the second correlation data (upper triangular matrix UTMA) calculated through the correlation data calculation processing (Step S1506); similarity calculation processing of calculating similarity between the second correlation data (upper triangular matrix UTMA) and the third correlation data (upper triangular matrix UTMB) extracted through the extraction processing (Step S1507); and identification processing of identifying, from the first correlation data, a second similar group Gr of specific first feature vectors being a calculation source of the third correlation data (upper triangular matrix UTMB) based on the similarity calculated through the similarity calculation processing (Step S1508), in the determination processing, the processor 201 is configured to determine a position in the network which is based on the specific first feature vectors included in the second similar group as a registration destination of the second node, and in the registration processing, the processor 201 is configured to register the second node (new node 110) to the registration destination determined through the determination processing, and couple the second node (new node 110) and a specific first node representing the specific first feature vector to each other with the second edge.

With this configuration, even when the first similar group Gq does not exist, the second similar group Gr can be searched for, and hence omission in the determination of the registration destination can be suppressed.

(4) Further, in Item (1), the registration apparatus 200 is configured to access attribute data (entry of personal DB 400 associated with personal ID 301) corresponding to the first feature vector V for each first feature vector V, and the processor 201 is configured to execute prediction processing of predicting an attribute corresponding to the second feature vector based on attribute data corresponding to the first feature vector represented by the first node existing in a range (circle 120) including the second node (new node 110) in the network 110 (Step S1404).

With this configuration, the state of the prediction target (for example, a person) indicated by the second node (new node 110) can be predicted through use of the attribute data corresponding to the first nodes around the second node.

(5) Further, in Item (1), the processor 201 is configured to execute generation processing of generating the network 101 (Step S803), and in the registration processing 201, the processor is configured to register, based on the similarity relationship among the third feature vectors, the second node (new node 110) representing the second feature vector to the network 101 generated through the generation processing, and couple the second node and the third node to each other with the second edge.

With this configuration, the registration apparatus 200 generates the network 101, and hence the first feature vectors V being the generation source of the network 101 can be hidden.

(6) Further, in Item (1), the first feature vector V is a vector indicating a feature of a living body of a person which is registered to the network 101 as the first node, and the second feature vector is a vector indicating a feature of a living body of a person which is unregistered to the network 101.

With this configuration, the registration apparatus 200 can be applied to the network 101 which is based on the living body data O. Consequently, a health state can objectively and precisely be predicted through use of the network 102 after the registration. Moreover, health support advice appropriate for each person can be provided through use of the network 102 after the registration.

It should be noted that this disclosure is not limited to the above-mentioned embodiments, and encompasses various modification examples and the equivalent configurations within the scope of the appended claims without departing from the gist of this disclosure. For example, the above-mentioned embodiments are described in detail for a better understanding of this disclosure, and this disclosure is not necessarily limited to what includes all the configurations that have been described. Further, a part of the configurations according to a given embodiment may be replaced by the configurations according to another embodiment. Further, the configurations according to another embodiment may be added to the configurations according to a given embodiment. Further, a part of the configurations according to each embodiment may be added to, deleted from, or replaced by another configuration.

Further, a part or entirety of the respective configurations, functions, processing modules, processing means, and the like that have been described may be implemented by hardware, for example, may be designed as an integrated circuit, or may be implemented by software by a processor interpreting and executing programs for implementing the respective functions.

The information on the programs, tables, files, and the like for implementing the respective functions can be stored in a storage device such as a memory, a hard disk drive, or a solid state drive (SSD) or a recording medium such as an IC card, an SD card, or a DVD.

Further, control lines and information lines that are assumed to be necessary for the sake of description are described, but not all the control lines and information lines that are necessary in terms of implementation are described. It may be considered that almost all the components are connected to one another in actuality.

What is claimed is:

1. A registration apparatus that reduces a calculation period that occurs when a machine learning network is updated to include a new node, the registration apparatus comprising:
   a memory;
   a communication interface that is communicatively coupled to the machine learning network, wherein the machine learning network includes a set of first nodes and first edges, the first nodes each representing a first feature vector including a plurality of elements, the first edges each coupling two first nodes representing two first feature vectors to each other based on two first feature vectors;
   a processor that is communicatively coupled to the memory and the communication interface,
   wherein the processor is configured to:
   obtain a second feature vector,
   obtain first correlation data, which represents correlation between each pair of first feature vectors in the machine learning network,
   determine whether a first similar group of specific third feature vectors exists in the set of third feature vectors, the specific third feature vectors satisfying a predetermined similarity condition,
   obtain correlation data, which represents correlation between each pair of the first feature vectors in the machine learning network,
   calculate a second correlation data indicating correlation between the second feature vector and each of the third feature vectors and correlation between each pair of the third feature vectors,
   extract, when the first similar group is determined not to exist, from the first correlation data, third correlation data having a same size as a size of the second correlation data calculated,
   calculate a similarity between the second correlation data and the third correlation data extracted,
   identify, from the first correlation data, a second similar group of specific first feature vectors being a calculation source of the third correlation data based on the similarity calculated,
   determine, as a registration destination for the new node, a position in the machine learning network based on the specific first feature vectors included in the second similar group and the specific third feature vectors included in the first similar group,
   register the new node to the registration destination, wherein the new node represents the second feature vector based on a similarity relationship among the third feature vectors in a set of the third feature vectors included in the set of first feature vectors, and
   couple the new node and a third node representing the third feature vector to each other with a second edge, wherein a number of the third feature vectors is smaller than a number of the first feature vectors.

2. The registration apparatus according to claim 1, wherein the processor is further configured to: access attribute data corresponding to the first feature vector for each of the first feature vectors, and
   predict an attribute corresponding to the second feature vector based on attribute data corresponding to the first feature vector represented by the first node existing in a range including the new node in the machine learning network.

3. The registration apparatus according to claim 1,
   wherein the first feature vector is a vector indicating a feature of a living body of a person which is registered to the machine learning network as the first node, and
   wherein the second feature vector is a vector indicating a feature of a living body of a person which is unregistered to the machine learning network.

4. A registration method that reduces a calculation period that occurs when a machine learning network is updated to include a new node, the registration method comprising:
   obtaining first correlation data, which represents correlation between each pair of first feature vectors in the machine learning network, wherein the machine learning network includes a set of first nodes and first edges, the first nodes each representing a first feature vector including a plurality of elements, the first edges each coupling two first nodes representing two first feature vectors to each other based on two first feature vectors;
   obtaining a second feature vector;
   determining whether a first similar group of specific third feature vectors exists in the set of third feature vectors, the specific third feature vectors satisfying a predetermined similarity condition;
   obtaining correlation data, which represents correlation between each pair of the first feature vectors in the machine learning network;
   calculating a second correlation data indicating correlation between the second feature vector and each of the third feature vectors and correlation between each pair of the third feature vectors;
   extracting, when the first similar group is determined not to exist, from the first correlation data, third correlation data having a same size as a size of the second correlation data calculated;
   calculating a similarity between the second correlation data and the third correlation data extracted;
   identifying, from the first correlation data, a second similar group of specific first feature vectors being a calculation source of the third correlation data based on the similarity calculated;
   determining, as a registration destination for the new node, a position in the machine learning network based on the specific first feature vectors included in the second similar group and the specific third feature vectors included in the first similar group;
   registering the new node to the registration destination, wherein the new node represents the second feature vector based on a similarity relationship among the third feature vectors in a set of the third feature vectors included in the set of first feature vectors, and
   coupling the new node and a third node representing the third feature vector to each other with a second edge, wherein a number of the third feature vectors is smaller than a number of the first feature vectors.

5. A non-transitory computer-readable recording medium having recorded thereon instructions that reduces a calculation period that occurs when a machine learning network is updated to include a new node, the instructions when executed by a processor cause the processor to execute a method comprising:
   obtaining first correlation data, which represents correlation between each pair of first feature vectors in the machine learning network, wherein the machine learning network includes a set of first nodes and first edges, the first nodes each representing a first feature vector including a plurality of elements, the first edges each coupling two first nodes representing two first feature vectors to each other based on two first feature vectors;

obtaining a second feature vector;

determining whether a first similar group of specific third feature vectors exists in the set of third feature vectors, the specific third feature vectors satisfying a predetermined similarity condition;

obtaining correlation data, which represents correlation between each pair of the first feature vectors in the machine learning network;

calculating a second correlation data indicating correlation between the second feature vector and each of the third feature vectors and correlation between each pair of the third feature vectors;

extracting, when the first similar group is determined not to exist, from the first correlation data, third correlation data having a same size as a size of the second correlation data calculated;

calculating a similarity between the second correlation data and the third correlation data extracted;

identifying, from the first correlation data, a second similar group of specific first feature vectors being a calculation source of the third correlation data based on the similarity calculated;

determining, as a registration destination for the new node, a position in the machine learning network based on the specific first feature vectors included in the second similar group and the specific third feature vectors included in the first similar group;

registering the new node to the registration destination, wherein the new node represents the second feature vector based on a similarity relationship among the third feature vectors in a set of the third feature vectors included in the set of first feature vectors, and coupling the new node and a third node representing the third feature vector to each other with a second edge, wherein a number of the third feature vectors is smaller than a number of the first feature vectors.

* * * * *